United States Patent
Meisberger

(10) Patent No.: US 6,627,911 B2
(45) Date of Patent: Sep. 30, 2003

(54) METHOD FOR DETERMINING A PARTICLE CONCENTRATION AND DEVICE FOR IMPLEMENTING THE METHOD

(75) Inventor: Artur Meisberger, Wendel (DE)

(73) Assignee: Fresenius HemoCare GmbH, Bad Homburg (DE)

( * ) Notice: Subject to any disclaimer, the term of this patent is extended or adjusted under 35 U.S.C. 154(b) by 148 days.

(21) Appl. No.: 09/779,921

(22) Filed: Feb. 8, 2001

(65) Prior Publication Data

US 2001/0032941 A1 Oct. 25, 2001

(30) Foreign Application Priority Data

Dec. 1, 1999 (DE) ......................... 199 58 729

(51) Int. Cl.$^7$ .............................. G01N 15/06
(52) U.S. Cl. ................ 250/574; 250/222.2; 356/337
(58) Field of Search .................. 250/222.2, 574, 250/575, 553, 573, 564, 565; 356/341, 318, 337, 336, 338, 339, 340, 343

(56) References Cited

U.S. PATENT DOCUMENTS 4,914,310 A * 4/1990 Jarofski ............... 250/574
5,241,369 A    8/1993 McNeil et al.
5,936,714 A    8/1999 Gibbs
6,088,087 A * 7/2000 Graves et al. ............ 356/39

FOREIGN PATENT DOCUMENTS

| DE | 197 35 328 | 3/1999 |
| EP | 074 428 | 3/1983 |
| EP | 0 562 630 | 9/1993 |
| WO | 97 22870 | 6/1997 |

* cited by examiner

Primary Examiner—Robert H. Kim
Assistant Examiner—Hoon K Song
(74) Attorney, Agent, or Firm—Kenyon & Kenyon

(57) ABSTRACT

A method for determining the particle concentration of a continuous medium in a receptacle, in which, a light beam from a light source is first directed through a particle-loaded, continuous medium, to the light-sensitive surface of a position-sensitive sensor, the light beam being so directed at the light-sensitive surface that the light scattered by the particles assuming, on the average, a different position than the unscattered light. The deviation of the midpoint of the scattered light on the light-sensitive surface from the midpoint of the unscattered light is subsequently determined, and this deviation is correlated to a specific particle concentration.

11 Claims, 2 Drawing Sheets

METHOD FOR DETERMINING A PARTICLE CONCENTRATION AND DEVICE FOR IMPLEMENTING THE METHOD

FIELD OF THE INVENTION

The present invention relates to a method for determining a particle concentration and, more particularly, for determining a particle concentration of a continuous medium in a container.

BACKGROUND OF THE INVENTION

A method of determining the particle concentration of dissolved substances using the scattering of laser light is disclosed in European Patent Application No. 7 44 28 A1, which is incorporated herein by reference. Blood components can be determined using such method. The quantitative determination of the particle concentration requires measuring the intensity of the primary beam and the intensity of the scattered radiation of the sample occurring at specific angles. The measured signals being corrected in order to compensate for altered physical conditions in the sample among the different measurements or within one measurement. The corrected measured signals are then assigned to the concentration of the system component to be determined. In accordance with the known teaching, the measurements are made within a scattering angle range in which there is a maximum dependence of the scattered-radiation intensity on the concentration of the respective component to be determined.

The sensor surfaces are typically comprised of a plurality of layers including a light-insensitive cover layer in which defined linear apertures are arranged to permit light to pass through to the light-sensitive layers situated underneath the cover layer. These defined linear apertures must be precisely assigned to the object to be measured as well as to the light source.

If there is a need to measure a medical suspension, such as blood, that is being passed through a tube, the tube must be precisely positioned with respect to the corresponding sensor surface having the linear apertures. This necessitates a precision-type design that is costly and prone to interference, to the extent that the tube is not securely fixed with respect to the sensor surface.

SUMMARY OF THE INVENTION

The object of the present invention is to provide an improved method of determining a particle concentration of a continuous medium that is adapted to be carried out using relatively simple measurement set-up and that is not readily susceptible to disturbances. It is a further object of the invention to accurately measure the particle concentration of a medical suspension, such as blood, that is contained on or passed through a tubular measurement receptacle (tube).

In accordance with the illustrative embodiments, demonstrating features and advantages of the present invention, there is provided a method for determining the particle concentration of a continuous medium in a container that includes the following steps: aligning a light beam from a light source through a particle-loaded, continuous medium, to the light-sensitive surface of a position-sensitive sensor, the light beam being so directed at the light-sensitive surface that the light scattered by the particles assuming, on average, a different position than the unscattered light; determining the deviation of the midpoint of the scattered light on the light-sensitive surface from the midpoint of the unscattered light on the light-sensitive surface; and correlating the deviation to the particle concentration.

The position-sensitive sensor is used on the basis of a large-surface area, light-sensitive surface. Such surface is preferably in the form of a PIN photodiode. Information can be provided about positioning through the use of at least two position dependent taps (contacts) even thought the light-sensitive surface has a homogeneous form. Using a sensor of this kind, the scattering behavior of the particle-loaded, continuous medium can be measured readily without a costly measurement set-up and with reduced susceptibility to failure. The measuring set-up is selected in such a way that the light beam altered by scattered light, on the average, assumes a different position than the light beam that is not scattered. This positional change, which is sensed by the light-sensitive surface of the position-sensitive sensor, can be drawn upon as a measure for the number of particles. That means that a corresponding positional change can be correlated to a specific particle concentration.

An important aspect of the method is that the light beam be directed at the light-sensitive surface in such a way that the light scattered by the particles assumes, on the average, a different position than the unscattered light. This can be achieved in accordance with a first variant of the embodiment in that the light beam is directed at right angles at the light-sensitive surface of the position-sensitive sensor, and in that the light-sensitive surface is partially covered so that the light beam striking upon this surface is at least partially covered or blocked.

Alternatively, the light beam can be directed at an angle (w) at the light-sensitive surface of the position-sensitive sensor.

In accordance with one preferred embodiment of the method according to the present invention, more than one light beam can be directed at the light-sensitive surface. These different light sources can also have different wavelengths. This makes it possible to determine the influence of the light scatterer on various wavelengths. If the light sources are simultaneously turned on, a differential signal can be detected, which can be used to determine, for example, whether the particles in question are scattering light substantially identically or variably.

A device for implementing the afore-mentioned method according to the present invention includes at least one light source, one receptacle for receiving or for directing the particle-loaded continuous medium, and a position-sensitive sensor having two current outputs configured at a distance from one another.

Using the device according to the present invention, it is possible to use one single, simply designed light sensor that makes use of only two electrical signals. In this manner, one can eliminate parameter scattering of components, as well as their temperature sensitivity and ageing effects.

In accordance with one preferred specific embodiment of the present invention, a simple light-emitting diode or a laser diode can be used as a light source without employing any additional optical systems.

Measurement receptacles of different types can be advantageously employed. They can be flat or in the form of a tube. Further, the receptacles can be rigid or flexible. For example, translucent tubes used to hold medical suspensions (e.g., blood) can be readily utilized.

The measuring method and the corresponding device exhibit a high sensitivity so that very small particle concentrations are able to be determined. Furthermore, there is no need to perform expensive adjustments on the light source and sensor since measuring signals can be received even when working with slightly shifted images.

Other objects, features and advantages of the invention will be readily apparent from the following detailed description of a preferred embodiment thereof taken in conjunction with the drawings.

BRIEF DESCRIPTION OF THE DRAWINGS

For the purpose of illustrating the invention, there is shown in the accompanying drawings forms which are presently preferred; it being understood that the invention is not intended to be limited to the precise arrangements and instrumentalities shown.

DETAILED DESCRIPTION OF THE PREFERRED EMBODIMENTS

Figure 1:
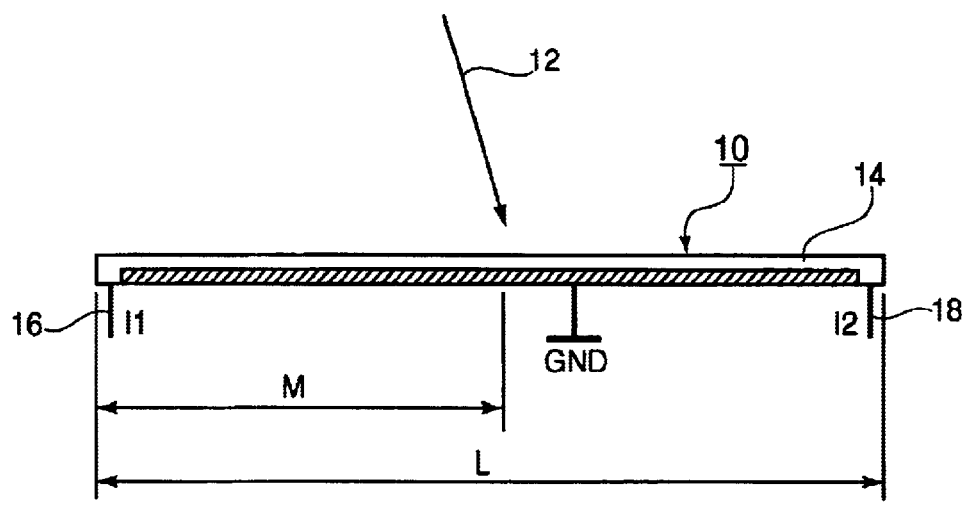
FIG. 1 is a schematic representation of a position-sensitive sensor in accordance with the present invention.

Referring now to the drawings in detail wherein like reference numerals have been used throughout the various figures to designate like elements, there is shown in FIG. 1 a schematic representation of a position-sensitive sensor 10. A light beam 12 from a light source (primary light beam) of the type known in the art is directed at a light-sensitive surface 14 of position-sensitive sensor 10. The sensor has two current outputs 16 and 18, arranged at distance L from one another, which are designated as current output $i_1$ (16) and current output $i_2$ (18) in FIG. 1. Position M of the incident light beam along the sensor surface can be determined with the assistance of current outputs 16 and 18. The partial currents are yielded according to the current-divider rule. The present invention makes use of this characteristic. Without the presence of light scatterers (e.g. cells or particles), the two currents 11 and 12 supply a position which can be taken as reference.

If the position is selected in such a way that, on average, the light beam altered by scattered light assumes a different position than the unscattered light beam, then this position change can be utilized as a measurement for the quantity of light scatterers. It is thus possible to determine the concentration of light scatterers. To that end, several reference measurements are performed beforehand, in terms of which a matrix is recorded which sets different concentrations against a position change of the scattered light. It is then possible to fall back on these reference values when measuring a particle-loaded, continuous medium so that the deviation measured in each case can be correlated to a corresponding particle concentration. It is also possible to adapt an already existing matrix by a calibration measurement for a measuring arrangement in order to be able to take small tolerances into account when working with substantially identical systems.

Figure 4:
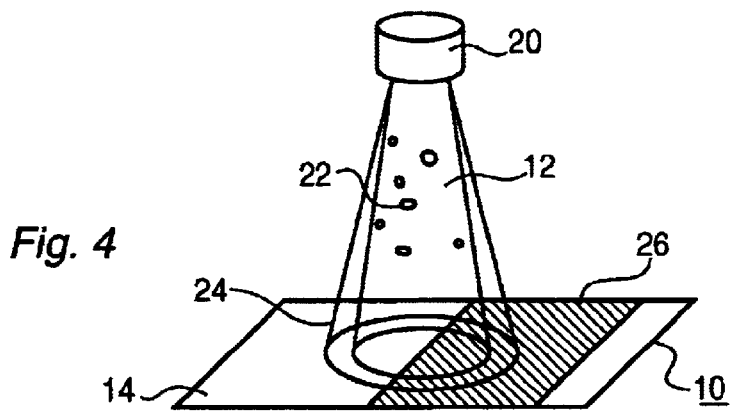
FIG. 4 is a schematic representation of a device in accordance with the present invention utilizing a flat measurement element.

A measurement set-up of a first specific embodiment is shown in principle in FIG. 4. There, a primary light beam 12 from a light source, e.g. a light-emitting diode 20, is directed at light-sensitive surface 14 of sensor 10, the light beam being aligned in a direction perpendicular to light-sensitive surface 14. Primary light beam 12 emerging from laser diode 20 is scattered by particles 22, in the present case cells, dwelling in the beam trajectory, resulting in a widened light beam 24. Due to the perpendicular alignment of light beams 12 and 24 with the light-sensitive surface 14, an identical computational midpoint results in each case, so that no shift of the midpoint of the primary beam to the midpoint of the light beam widened by the scattering takes place on the light-sensitive surface. A part of light-sensitive surface 14 is covered by a cover 26. Through this, as shown in FIG. 4, only a part of the light beam is directed at light-sensitive surface 14.

Figure 2:
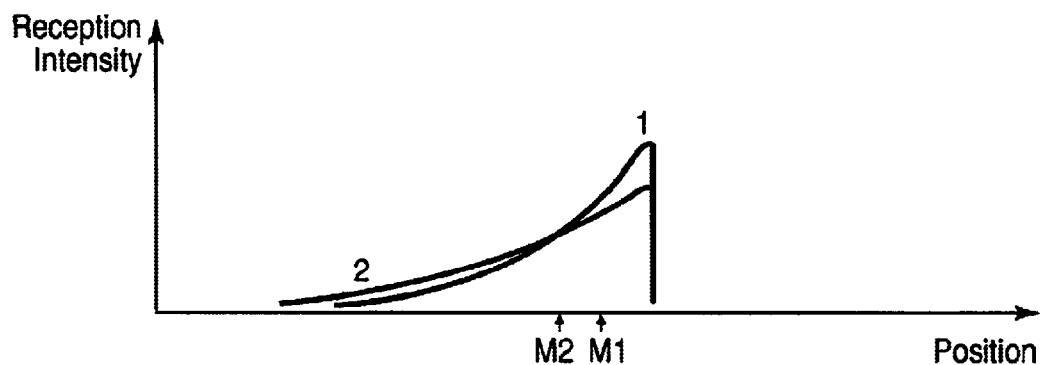
FIG. 2 is a diagram depicting the reception intensity of the intercepted light as a function of the position on the position-sensitive sensor, the reception relationships of a device according to FIG. 4.

With reference to the recorded reception intensity, a distribution results that is specific to the position on the light-sensitive sensor, as shown by way of example in FIG. 2. Curve 1 shows the reception intensity of the primary beam, for which a computational midpoint is yielded at M1. The reception intensity of widened light beam 24 is shown by curve 2, for which a computational midpoint M2 results. Naturally, the reception intensity goes back to zero at the boundary line of cover 26. The positions of the midpoints can be determined according to the current-divider rule using the following formula:

$$(i_1-i_2)/(i_1+i_2)=1-2(M/L).$$

Figure 3:
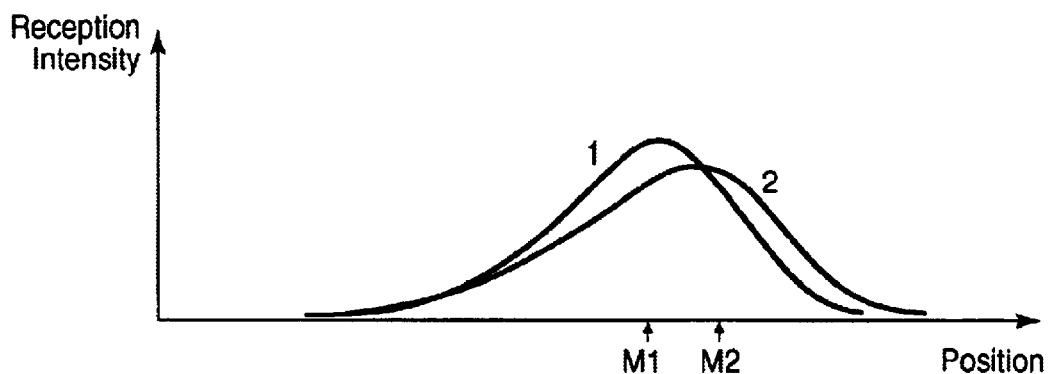
FIG. 3 is a diagram depicting the reception intensity of the intercepted light as a function of the position on the position-sensitive sensor, the reception relationships of a device according to FIG. 5.
Figure 5:
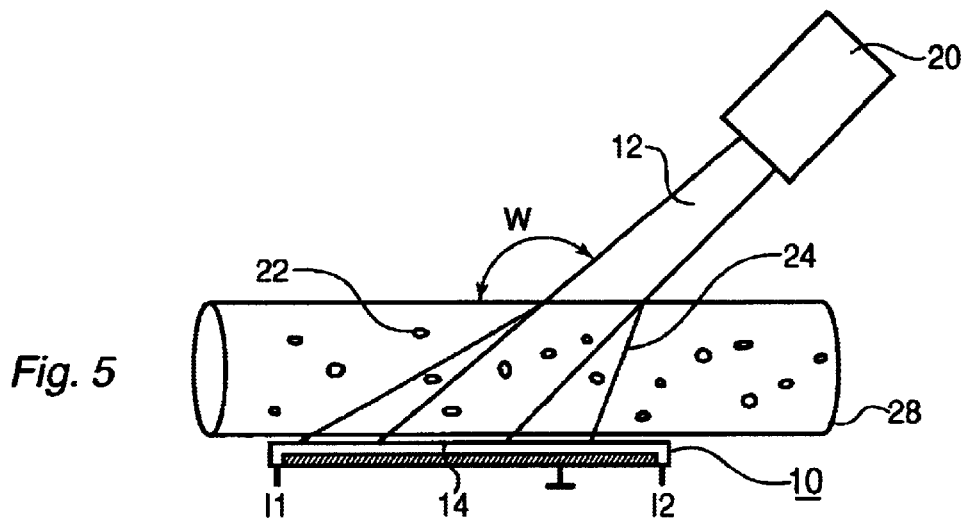
FIG. 5 is a schematic representation of a device in accordance with an alternate embodiment of the present invention and utilizing a tubular measurement receptacle.

FIG. 5 shows a second specific embodiment. Here, primary light beam 12 emerging from laser diode 20 is aligned diagonally, at an angle w, with respect to sensor surface 14 of sensor 10. Arranged between light-emitting diode 20 and light-sensitive surface 14 is a tubing line 28 as a receptacle for cells 22 whose concentration is to be determined. Primary beam 12 is widened by scattering cells 22 thereby resulting in widened light beam 24. The resulting light distribution on light-sensitive surface 14 of sensor 10 is represented in FIG. 3. Here, curve 1 corresponds to the reception intensity of the primary beam, and curve 2 corresponds to the reception intensity of widened light beam 24. M1 is the computational midpoint which belongs to curve 1 and thus to primary beam 12, while M2 is the midpoint of reception-intensity curve 2 of widened light beam 24.

Figure 6:
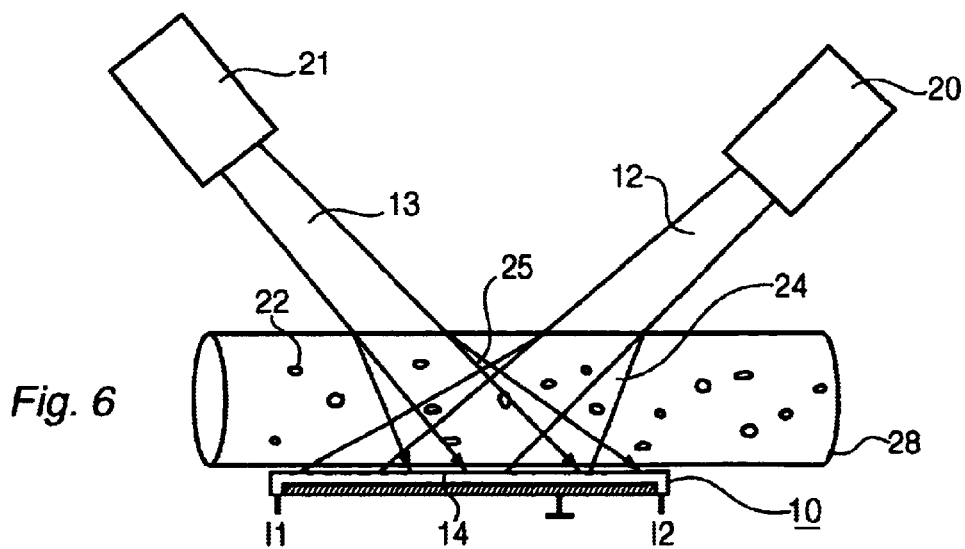
FIG. 6 is a schematic representation of a device in accordance with another embodiment of the present invention and utilizing a tubular measurement receptacle.

In the arrangement shown in FIG. 6, two laser diodes 20 and 21 are selected as light sources, each emitting laser light of a different wavelength as primary beams 12 and 13. Primary light beam 12 is widened by cells 22 into light beam 24, while primary light beam 13 is widened into light beam 25. Because beams 12 and 13 have different wavelengths, the influence of the light scatterers on the different wavelengths can be determined. If laser diodes 20 and 21 are switched on simultaneously, a differential signal can be ascertained. Using this differential signal, it is possible to determine, for example, whether the light scatterers are substantially identical or different.

Instead of the specific embodiment having two current outputs shown in FIG. 1, it is also possible to use a uniplanar photodiode with 2×2 outputs. Midpoint M can then be ascertained two-dimensionally.

The present invention may be embodied in other forms without departing from the spirit or essential attributes thereof and accordingly reference should be made to the claims rather than to the foregoing specification as indicating the scope thereof.

What is claimed is:

1. A method for determining the particle concentration of a continuous medium in a receptacle comprising the steps of:
    aligning a light beam from a light source through a particle containing, continuous medium to a light-sensitive surface of a position-sensitive sensor, the light beam being directed at the light-sensitive surface so that the light scattered by the particles assumes, on average, a different position than the unscattered light;
    determining a deviation of a position of a midpoint of the scattered light on the light-sensitive surface from a position of a midpoint of the unscattered light on the light-sensitive surface; and
    correlating the deviation to the particle concentration.

2. The method of claim 1 wherein the light beam is directed at right angles at the light-sensitive surface of the position-sensitive sensor, and wherein the light-sensitive surface is partially covered.

3. The method of claim 1 wherein the light beam is directed at an angle at the light-sensitive surface of the position-sensitive sensor.

4. The method of claim 1 wherein at least two light beams are directed at the light-sensitive surface.

5. The method of claim 4 wherein the at least two light beams have at least two partially different wavelengths.

6. The method of claim 1 wherein the continuous medium is a medical suspension.

7. The method of claim 1 wherein the continuous medium includes a plurality of blood particles.

8. A device for determining the particle concentration of a continuous medium in a receptacle comprising:
    at least one light source;
    a receptacle for receiving or directing a continuous medium, the continuous medium including a plurality of particles; and
    a position-sensitive sensor having a light-sensitive surface, and two current outputs configured at a distance from one another, so as to determine a deviation in position of light from the at least one light source when scattered by the plurality of particles in the continuous medium.

9. The device of claim 8 wherein the at least one light source is a laser diode or a light-emitting diode.

10. The device of claim 8 wherein the receptacle is a tube and the continuous medium is a medical suspension.

11. The device of claim 10 wherein the medical suspension includes a plurality of blood particles.

* * * * *